United States Patent
Zhao et al.

(10) Patent No.: US 11,840,525 B2
(45) Date of Patent: Dec. 12, 2023

(54) USE OF AURKB SMALL-MOLECULE INHIBITORS FOR TREATMENT OF NON-SMALL CELL LUNG CANCER

(71) Applicant: Nanjing China-Australia Institute of Translational Medicine Co.Ltd., Jiangsu (CN)

(72) Inventors: Quan Zhao, Jiangsu (CN); Renxiang Tan, Jiangsu (CN); Yadong Wang, Jiangsu (CN); Liping Lin, Jiangsu (CN)

(73) Assignee: Nanjing China-Australia Institute of Translational Medicine Co. Ltd., Nanjing (CN)

( * ) Notice: Subject to any disclaimer, the term of this patent is extended or adjusted under 35 U.S.C. 154(b) by 252 days.

(21) Appl. No.: 17/384,765

(22) Filed: Jul. 25, 2021

(65) Prior Publication Data

US 2021/0347764 A1    Nov. 11, 2021

Related U.S. Application Data

(60) Division of application No. 16/408,549, filed on May 10, 2019, now abandoned, and a continuation of application No. PCT/CN2017/110436, filed on Nov. 10, 2017.

(30) Foreign Application Priority Data

Nov. 11, 2016 (CN) .......................... 201610993691.9

(51) Int. Cl.
*C07D 403/14* (2006.01)
*A61P 35/00* (2006.01)

(52) U.S. Cl.
CPC ............ *C07D 403/14* (2013.01); *A61P 35/00* (2018.01)

(58) Field of Classification Search
CPC .................................................. C07D 403/14
See application file for complete search history.

(56) References Cited

U.S. PATENT DOCUMENTS 8,399,502 B2    3/2013    Jong et al.
2010/0069355 A1    3/2010    Jong et al.

FOREIGN PATENT DOCUMENTS

CN    106565587 A    4/2017
WO    2005107747 A2    11/2005

OTHER PUBLICATIONS

Chang, Yuchen et al. "Cytostatic and Antiestrogenic Effects of 2-(Indol-3-ylmethyl)-3,3,-diindolylmethane,a Major In Vivo Product of Dietary Indole-3-carbinol" Biochemical Pharmacology, vol. 58, pp. 825-834, Dec. 31, 1999.
Wan-Ru Chao et al. "Computer-Aided Rational Drug Design A Novel Agent(SR13668) Designed to Mimic the Unique Anticancer Mechanisms of Dietary Indole-3-Carbinol to Block AkT Signaling" J.Med.Chem, vol. 50, No. 15; pp. 3412-3415, Dec. 31, 2007.

*Primary Examiner* — Brian E McDowell

(57) ABSTRACT

Disclosed is a use of a small-molecule AURKB inhibitor for treatment of non-small cell lung cancer. The small-molecule AURKB inhibitor is directed to a diindolylmethane compound of formula (I-a) or a solvate, a N-oxide or a pharmaceutically acceptable salt thereof,

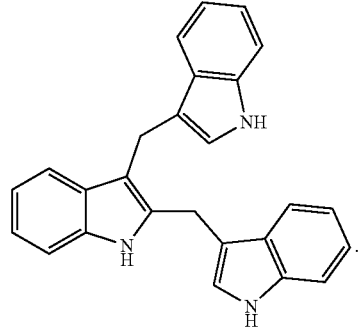

(I-a)

1 Claim, 22 Drawing Sheets
Specification includes a Sequence Listing.

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: synthetic

<400> SEQUENCE: 1
cgcggatcca tggcccagaa ggagaactcc                              30

<210> SEQ ID NO 2
<211> LENGTH: 30
<212> TYPE: DNA
<213> ORGANISM: Homo sapiens

<400> SEQUENCE: 2
cgcctcgagt caggcgacag attgaagggc                              30

<210> SEQ ID NO 3
<211> LENGTH: 19
<212> TYPE: DNA
<213> ORGANISM: Artificial Sequence
<220> FEATURE:
<223> OTHER INFORMATION: synthetic

<400> SEQUENCE: 3
cgtgattcac agagacata                                          19

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
cgctcaaggt cctcttcaa                                          19

<210> SEQ ID NO 5
<211> LENGTH: 1246
<212> TYPE: DNA
<213> ORGANISM: Artificial Sequence
<220> FEATURE:

<223> OTHER INFORMATION: synthetic

<400> SEQUENCE: 5

```
agttgtttgc gggcggccgg gagagtagca gtgccttgga ccccagctct cctccccctt    60
tctctctaag gatggcccag aaggagaact cctaccsctg gccctacggc cgacagacgg   120
ctccatctgg cctgagcacc ctgccccagc gagtcctccg gaaagagcct gtcaccccat   180
ctgcacttgt cctcatgagc cgctccaatg tccagcccac agctgcccct ggccagaagg   240
tgatggagaa tagcagtggg acacccgaca tcttaaccag gcggcacttc acaattgatg   300
actttgagat tgggcgtcct ctgggcaaag gcaagtttgg aaacgtgtac ttggctcggg   360
agaagaaaag ccatttcatc gtggcgctca aggtcctctt caagtcccag atagagaagg   420
agggcgtgga gcatcagctg cgcagagaga tcgaaatcca ggcccacctg caccatccca   480
acatcctgcg tctctacaac tattttttatg accggaggag gatctacttg attctagagt   540
atgccccccg cggggagctc tacaaggagc tgcagaagag ctgcacattt gacgagcagc   600
gaacagccac gatcatggag gagttggcag atgctctaat gtactgccat gggaagaagg   660
tgattcacag agacataaag ccagaaaatc tgctcttagg gctcaaggga gagctgaaga   720
ttgctgactt cggctggtct gtgcatgcgc cctcccctgag gaggaagaca atgtgtggca   780
ccctggacta cctgccccca gagatgattg aggggcgcat gcacaatgag aaggtggatc   840
tgtggtgcat tggagtgctt tgctatgagc tgctggtggg gaacccaccc tttgagagtg   900
catcacacaa cgagacctat cgccgcatcg tcaaggtgga cctaaagttc cccgcttccg   960
tgcccatggg agcccaggac ctcatctcca aactgctcag gcataacccc tcggaacggc  1020
tgcccctggc ccaggtctca gcccaccctt gggtccgggc caactctcgg agggtgctgc  1080
ctccctctgc ccttcaatct gtcgcctgat ggtccctgtc attcactcgg gtgcgtgtgt  1140
ttgtatgtct gtgtatgtat agggggaaaga agggatccct aactgttccc ttatctgttt  1200
tctacctcct cctttgttta ataaaggctg aagcttttg tactca                  1246
```

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6

```
acatcttaac gcggcacttc                                                20
```

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7

```
atgaaatggc ttttcttctc c                                              21
```

<210> SEQ ID NO 8
<211> LENGTH: 19
<212> TYPE: DNA
<213> ORGANISM: Artificial Sequence
<220> FEATURE:
<223> OTHER INFORMATION: synthetic

<400> SEQUENCE: 8
agactcggta tgacacttc                                                19

<210> SEQ ID NO 9
<211> LENGTH: 19
<212> TYPE: DNA
<213> ORGANISM: Artifical Sequence
<220> FEATURE:
<223> OTHER INFORMATION: synthetic

<400> SEQUENCE: 9
cactggatgt tgttcttgg                                                19

<210> SEQ ID NO 10
<211> LENGTH: 345
<212> TYPE: PRT
<213> ORGANISM: Homo sapiens

<400> SEQUENCE: 10

Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg Arg His Phe Thr Ile Asp Asp Phe Glu Ile
65                  70                  75                  80

Gly Arg Pro Leu Gly Lys Gly Lys Phe Gly Asn Val Tyr Leu Ala Arg
                85                  90                  95

Glu Lys Lys Ser His Phe Ile Val Ala Leu Lys Val Leu Phe Lys Ser
            100                 105                 110

Gln Ile Glu Lys Glu Gly Val Glu His Gln Leu Arg Arg Glu Ile Glu
        115                 120                 125

Ile Gln Ala His Leu His His Pro Asn Ile Leu Arg Leu Tyr Asn Tyr
    130                 135                 140

Phe Tyr Asp Arg Arg Arg Ile Tyr Leu Ile Leu Glu Tyr Ala Pro Arg
145                 150                 155                 160

Gly Glu Leu Tyr Lys Glu Leu Gln Lys Ser Cys Thr Phe Asp Glu Gln
                165                 170                 175

Arg Thr Ala Thr Ile Met Glu Glu Leu Ala Asp Ala Leu Met Tyr Cys
            180                 185                 190

His Gly Lys Lys Val Ile His Arg Asp Ile Lys Pro Glu Asn Leu Leu
        195                 200                 205

Leu Gly Leu Lys Gly Glu Leu Lys Ile Ala Asp Phe Gly Trp Ser Val
    210                 215                 220

His Ala Pro Ser Leu Arg Arg Lys Thr Met Cys Gly Thr Leu Asp Tyr
225                 230                 235                 240

Leu Pro Pro Glu Met Ile Glu Gly Arg Met His Asn Glu Lys Val Asp
                245                 250                 255

Leu Trp Cys Ile Gly Val Leu Cys Tyr Glu Leu Leu Val Gly Asn Pro
            260                 265                 270

Pro Phe Glu Ser Ala Ser His Asn Glu Thr Tyr Arg Arg Ile Val Lys
        275                 280                 285

| | | | | | | | | | | | | | | |
|---|---|---|---|---|---|---|---|---|---|---|---|---|---|---|
| Val | Asp | Leu | Lys | Phe | Pro | Ala | Ser | Val | Pro | Met | Gly | Ala | Gln | Asp | Leu |
| | 290 | | | | 295 | | | | 300 | | | | | |
| Ile | Ser | Lys | Leu | Leu | Arg | His | Asn | Pro | Ser | Glu | Arg | Leu | Pro | Leu | Ala |
| 305 | | | | 310 | | | | | 315 | | | | | 320 | |
| Gln | Val | Ser | Ala | His | Pro | Trp | Val | Arg | Ala | Asn | Ser | Arg | Arg | Val | Leu |
| | | | 325 | | | | | 330 | | | | | 335 | | |
| Pro | Pro | Ser | Ala | Leu | Gln | Ser | Val | Ala | | | | | | | |
| | | 340 | | | | 345 | | | | | | | | | |

USE OF AURKB SMALL-MOLECULE INHIBITORS FOR TREATMENT OF NON-SMALL CELL LUNG CANCER

CROSS-REFERENCE TO RELATED APPLICATIONS

This application is a divisional application of U.S. patent application Ser. No. 16/408,549, filed on May 10, 2019, which is a continuation of International Patent Application No. PCT/CN2017/110436, filed on Nov. 10, 2017, which claims the benefit of priority from Chinese application No. 201610993691.9, filed on Nov. 11, 2016. The content of the aforementioned application, including any intervening amendments thereto, are incorporated herein by reference.

TECHNICAL FIELD

This application relates to pharmaceutical chemistry, and more particularly to a use of a diindolylmethane compound for treatment of non-small cell lung cancer. The diindolylmethane compound can be used as an AURKB inhibitor and thus can be used for treating diseases and symptoms caused by AURKB-related abnormal cell function and behavior.

BACKGROUND

Cancer is one of the leading causes of morbidity and mortality worldwide. According to the data revealed by the International Cancer Research Institute in 2014, the number of the cases suffering from cancer is increasing sharply worldwide. There are about 8 million cases died from cancer every year and the mortality resulted from lung cancer ranks first. In addition, the number of new cases of lung cancer in China is the most in the world, which greatly threatens the health and life of our people. The cancer mortality can be reduced if it is diagnosed and treated in time. Although a great progress has been made in the identification of tumor markers and improvement of methods for treating tumors, such as the development of circulating microRNA, carcinoembryonic antigen (CEA) and new chemical reagents, and the improvement in surgical operation, which greatly improves the efficiency in diagnosis and treatment of tumors, it is still limited for the discovery and treatment of cancers. So far, researches are mainly focused on finding a new tumor marker and a new anti-tumor drug with low toxicity, high efficiency and high specificity.

Protein aurora kinase B (AURKB), pertaining to the protein kinase family, is a serine/threonine kinase which plays an important role in the regulation of mitosis and the formation of tumors including lung cancer, breast cancer, prostate cancer, bladder cancer, head and neck cancer, liver cancer, cerebral cancer and ovarian cancer. Studies have shown that in the mitosis, AURKB is involved in many processes such as centrosome maturation and separation, spindle assembly and maintenance, chromosome segregation and cytokinesis. AURKB combines with survivin, broealin and INCENP proteins to form a chromosomal passenger complex (CPC), and then positioned on the centromere and the centrosome to regulate the adhesion of tubulin and the segregation of chromosome, thereby regulating the cell division. Currently, a large number of small-molecule inhibitors targeting AURKB have been reported, of which about 30 small-molecule inhibitors have been used in preclinical or clinical trial. Although some of them show desired effects in the treatment of leukemia, they are not very ideal for treating solid tumors including lung cancer as shown in the clinical results. It may be explained by that most inhibitors can hardly enter solid tumor through blood and the drug at a low dose may fail to reach the lesion, while the high-dose administration may lead to obvious side effects such as fever and diarrhea. Therefore, there is an urgent need to develop a natural small-molecule inhibitor with low toxicity, high efficiency and specificity and capable of inhibiting the activity of AURKB and its signaling pathway, which can be applied in the development of a new effective anti-tumor drug.

SUMMARY

An object of the invention is to provide a small-molecule AURKB (with an amino acid sequence shown in SEQ ID NO: 10) inhibitor (TZ47) which can inhibit the proliferation of various tumor cells and induce their apoptosis and autophagy.

The technical solutions of the invention are described as follows.

In a first aspect, this application discloses a small-molecule AURKB inhibitor (TZ47), which is a diindolylmethane compound of formula (I), or a stereoisomer, a tautomer, a solvate, a prodrug, an N-oxide or a pharmaceutically acceptable salt thereof:

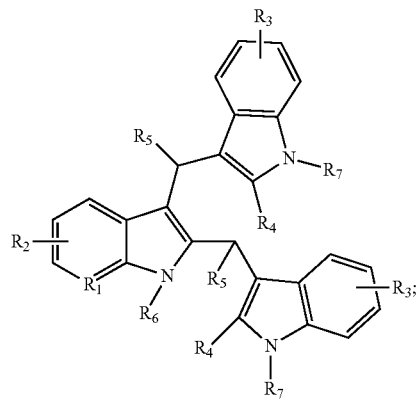

wherein:

$R_1$ is CH or a heteroatom selected from N, O, S or N→O;

$R_2$ and $R_3$ each are independently hydrogen, unsubstituted saturated or unsaturated $C_1$~$C_6$ linear alkyl, branched alkyl, alicyclic hydrocarbon, aromatic ring or heteroaromatic ring; saturated or unsaturated $C_1$~$C_6$ linear alkyl, branched alkyl, alicyclic hydrocarbon, aromatic ring or heteroaromatic ring substituted by alcohol, amino, nitrogen, sulfur, oxygen, halogen or carbonyl; or halogen, hydroxyl, nitro group, cyano group, amino, trifluoromethyl, trichloromethyl, tribromomethyl or triiodomethyl, or triiodomethyl;

each $R_4$ is independently hydrogen, unsubstituted saturated or unsaturated $C_1$~$C_6$ linear alkyl, branched alkyl, alicyclic hydrocarbon, aromatic ring or heteroaromatic ring; or saturated or unsaturated $C_1$~$C_6$ linear alkyl, branched alkyl, alicyclic hydrocarbon, aromatic ring or heteroaromatic ring substituted by alcohol, amino, nitrogen, sulfur, oxygen, halogen or carbonyl; or halogen, hydroxyl, nitro group, cyano group, amino, carboxyl, aldehyde group, ester group, trifluoromethyl, trichloromethyl, tribromomethyl, triiodomethyl or trimethylsilyl;

each $R_5$ and $R_7$ are independently hydrogen, unsubstituted saturated or unsaturated $C_1$~$C_6$ linear alkyl, branched alkyl, alicyclic hydrocarbon, aromatic ring or heteroaromatic ring; or saturated or unsaturated $C_1$~$C_6$ linear alkyl, branched alkyl, alicyclic hydrocarbon, aromatic ring or heteroaromatic ring substituted by alcohol, amino, nitrogen, sulfur, oxygen, halogen or carbonyl; or halogen, hydroxyl, nitro group, cyano group, amino, carboxyl, aldehyde group, ester group, trifluoromethyl, tri chloromethyl, tribromomethyl, triiodomethyl, trimethylsilyl, phosphate or sulfate; and $R_6$ is hydrogen, unsubstituted saturated and unsaturated $C_1$~$C_6$ linear alkyl, branched alkyl, alicyclic hydrocarbon, aromatic ring or heteroaromatic ring; saturated and unsaturated $C_1$~$C_6$ linear alkyl, branched alkyl, alicyclic hydrocarbon, aromatic ring or heteroaromatic ring substituted by alcohol, amino, nitrogen, sulfur, oxygen, halogen or carbonyl; or halogen, hydroxyl, nitro group, cyano group, amino, carboxyl, aldehyde group, ester group, trifluoromethyl, trichloromethyl, tribromomethyl, triiodomethyl, trimethylsilyl, phosphate or sulfate.

In a second aspect, this application discloses a method of preparing the diindolylmethane compound of formula (I), or a stereoisomer, a tautomer, a solvate, a prodrug, an N-oxide or a pharmaceutically acceptable salt thereof, comprising:

reacting compound 1 with compound 2 in the presence of $(CF_3SO_3)_3Sc$ under nitrogen protection to produce the diindolylmethane compound of formula (I);

wherein the reaction is represented by the following reaction scheme:

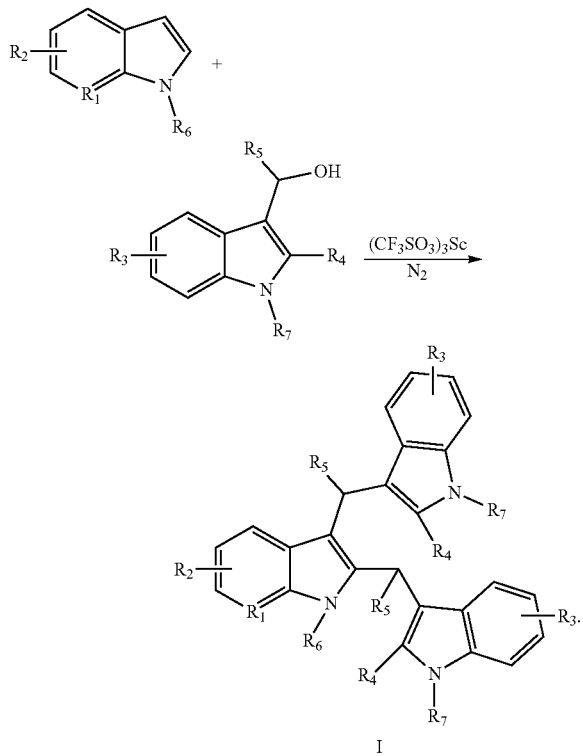

I

In a third aspect, this application discloses A method of treating a disease or symptom caused by AURKB-related abnormal cell growth, function or behavior in a patient, comprising: administering to the patient an effective amount of the diindolylmethane compound of claim 1, or a stereoisomer, a tautomer, a solvate, a prodrug, an N-oxide or a pharmaceutically acceptable salt thereof, or a composition comprising the same.

In an embodiment, the disease or symptom comprises abnormal proliferative disease comprising cancer, immune disease, cardiovascular disease, viral infection, inflammation, metabolic/endocrine disorder comprising diabetes and obesity, and neurologic disease.

In an embodiment, the cancer is selected from the group consisting of non-small cell lung cancer, acute and chronic leukemia, liver cancer, gastric cancer, colorectal cancer, ovarian cancer and melanoma.

In a forth aspect, this application discloses a pharmaceutical composition for treating a disease or symptom caused by AURKB-related abnormal cell growth, function or behavior, which comprises a therapeutically effective amount of the diindolylmethane compound of formula (I), or a stereoisomer, a tautomer, a solvate, a prodrug, an N-oxide or a pharmaceutically acceptable salt thereof as an active ingredient, and a pharmaceutically acceptable carrier, auxiliary or excipient.

In a fifth aspect, this application discloses a method of treating non-small cell lung cancer in a patient, comprising: administering to the patient an effective amount of a diindolylmethane compound of formula (I-a), or a stereoisomer, a tautomer, a solvate, a prodrug, an N-oxide or a pharmaceutically acceptable salt thereof,

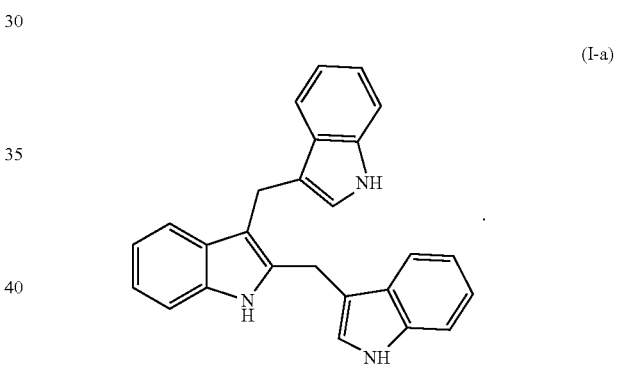

(I-a)

The small-molecule AURKB inhibitor of the invention can inhibit the AURKB activity to lower the phosphorylation level of histone H3S10 and inhibit the expression of E2F2 gene, effectively inhibiting the proliferation of tumor cells, activating the cell apoptosis and autophagy and inducing the cell death. Thus, this invention can be applied to the preparation of a drug for treating a cancer, especially the non-small cell lung cancer.

This invention further provides an anti-tumor pharmaceutical composition, which contains the small-molecule AURKB inhibitor as an active ingredient and a pharmaceutically acceptable carrier and excipient.

The small-molecule AURKB inhibitor can be administered alone or made into a preparation with more than one acceptable carrier such as a solvent and a diluent for administration. The preparation can be orally administered, such as tablets, capsules, dispersible powder, and granules; and can also be administered by injection, such as freeze-dried powder injections. Various preparations of the pharmaceutical composition of the invention can be prepared according to the methods well known in the pharmaceutical field.

Compared to the prior art, this invention has the following advantages.

1. The small-molecule AURKB inhibitor of the invention can be isolated from the natural product of a plant, and can also be prepared by biosynthesis or microbial fermentation. This process involves simple reaction and high yield. Besides, the product is easy to be purified stored.
2. The small-molecule AURKB inhibitor identified by the invention has low toxicity to normal cells and can significantly inhibit the expression of the downstream gene E2F2 mediated by the phosphorylation of the AURKB substrate histone H3S10. Therefore, the small-molecule AURKB inhibitor can effectively inhibit the proliferation of many tumor cells and induce the apoptosis of tumor cells, suitable for the development of a new anti-tumor drug.

DETAILED DESCRIPTION OF EMBODIMENTS

The present application will be further illustrated with reference to the experiments.

Example 1

Figure 1A:
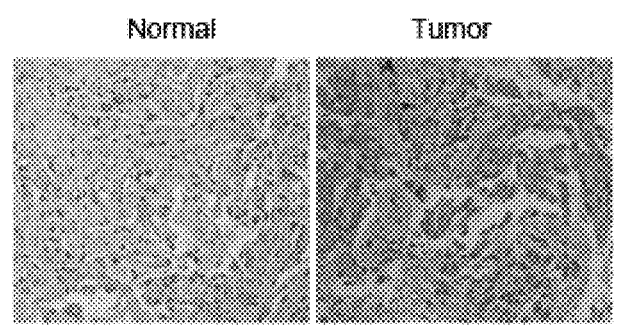
FIGS. 1A-1B show the protein level of AURKB in a tumor tissue sample from a patient suffering from non-small cell lung cancer by immunohistochemical and Western blot assays.
Figure 1B:
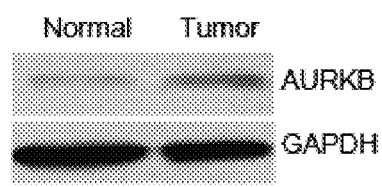
Figure 2:
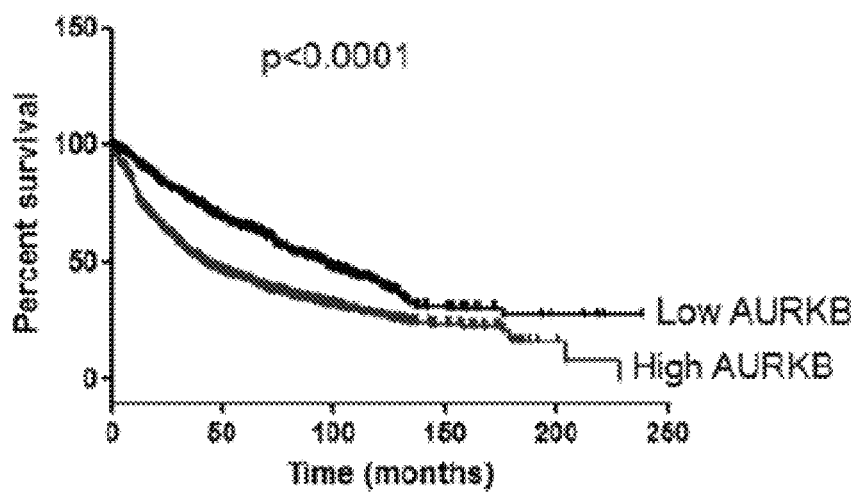
FIG. 2 shows the negative correlation between the expression level of AURKB and the survival rate of lung cancer patients.

This invention utilized immunohistochemical technology to analyze the expression levels of AURKB in tumor specimens and normal para-cancerous tissues of a patient suffering from non-small cell lung cancer. The results showed that the expression levels of AURKB in tumor tissues of the lung cancer patient were significantly up-regulated (see FIGS. 1A-1B), and were negatively correlated with the survival rate of patients (see FIG. 2).

Specific steps were shown below.

a. Paraffin embedding and sectioning

1) Fixing

Fresh tissue samples were fixed in 4% paraformaldehyde for 24 h.

2) Dehydration

The fixed tissues were dehydrated by immersion sequentially in 50% ethanol for 30 min, 70% ethanol for 30 min, 80% ethanol for 1 h, 85% ethanol for 30 min, 90% ethanol for 15 min, 95% ethanol for 15 min, 100% ethanol for 15 min and a mixture of ethanol/xylene (1:1) for 20 min.

3) Transparency

The dehydrated tissues were placed in xylene for 3 min, and then in a mixture of xylene/paraffin (1:1) at 60° C. for 15 min.

4) Wax immersion

The transparent tissues were immersed in paraffin I at 60° C. for 20 min, and in paraffin II at 60° C. for 15 min.

5) Embedding

The paraffin was melted and poured into a mold at an appropriate amount. The tissue samples were placed in the middle of the mold with a tweezers and then the mold was filled with paraffin. After the paraffin was cooled down, the mold was placed in a refrigerator at 4° C. overnight to allow the paraffin for complete solidification.

6) Sectioning

The paraffin block was removed from the mold, trimmed and sectioned into slices with a thickness of about 5 μm using radical microtome. Then the paraffin slices were placed in water at 42° C. to flatten and the flattened slices were collected by glass slides and dried at room temperature for 2 h.

b. immunohistochemistry

1) Deparaffination and hydration

The paraffin slices were deparaffinized and hydrated by immersions sequentially in xylene I for 15 min, xylene II for 15 min, 100% ethanol for 3 min, 95% ethanol for 3 min, 90% ethanol for 3 min, 80% ethanol for 3 min, 70% ethanol for 3 min, 60% ethanol for 3 min, 50% ethanol for 3 min, ddH$_2$O for 3 min, 3% 11202 for 10 min and ddH$_2$O for 5 min.

2) Antigen retrieval

The hydrated tissue slices were placed in a sodium citrate retrieval solution at 94° C. for 15 min, removed and cooled naturally at room temperature.

3) Incubation of primary antibody

The tissue slices were dropwise added with a 5% BSA blocking buffer and kept at room temperature for 20 min. The remaining blocking buffer was removed and then the primary antibody (prepared by anti-AURKB (Abeam) and 5% blocking buffer in a ratio of 1:100) was added and incubated in a wet box at 4° C. overnight.

4) Washing

The excessive primary antibody was removed by washing with PBS 3 times for 5 min each.

5) Incubation of secondary antibody

A biotin-coupled secondary antibody (prepared by an antibody and 5% BSA in a ratio of 1:100) was dropwise added and incubated at 37° C. for 1 h.

6) Washing

The excessive secondary antibody was removed by washing with PBS 3 times for 5 min each.

7) The tissue slices were dropwise added with a SABC (streptavidin-biotin complex) solution, kept at 37° C. for 40 min and washed with PBS 3 times for 5 min each.

8) DAB color development 1 mL of ddH$_2$O was added to a DAB dye solution from a kit, mixed uniformly, dropwise added to the slices and observed for the color development using a microscope. When obvious brown occurred, that is, a significant positive signal was observed, the slices were washed with water to terminate the reaction, avoiding excessive color development.

9) Hematoxylin counterstaining

The tissue slices were placed in a water-soluble hematoxylin for 10 s and washed with water to colorless.

10) Dehydration and mounting

The slices were dehydrated by immersions sequentially in 95% ethanol for 3 min, 100% ethanol for 3 min and xylene for 10 min, mounted with neutral balsam, air dried overnight, and stored at room temperature for observation of the tissue morphology.

c. Western blot assay

The cell lysis buffer was prepared as follows.

| | |
|---|---|
| 50 mM | Tris-HCl pH 8.0 |
| 150 mM | NaCl |
| 1 mM | EDTA |
| 1% | Triton X-100 |
| 10% | Glycerol |

The normal paracancerous tissues and tumor tissues of the patient were collected, cut into small pieces and ground in liquid nitrogen. The ground tissues were then added with 1 mL of the cell lysis buffer and 1× protease inhibitor, placed on ice for 15 min and then centrifuged at 12,000 rpm and 4° C. for 10 min. The supernatant, i.e., the lysed cell protein liquid, was collected.

1) The electrophoresis apparatus was prepared, and a running gel and a stacking gel were prepared in advance. The boiled protein liquid was subjected to SDS-PAGE (the concentration of the running gel depended on the molecular weight of the target protein), where the electrophoresis was performed at 90 V for 30 min and then at 120 V for 1 h.

2) The resulting SDS-polyacrylamide gel was immersed in 1×transfer buffer, and then 2 pieces of filter paper and one piece of PVDF membrane involving similar size were obtained by cutting, where their sizes depended on the size of the sliced gel. The PVDF membrane needed to be activated in methanol for 10 min and the filter paper should be immersed in 1×transfer buffer in advance.

3) The semi-dry transfer system was placed, from the top down, sequentially with filter paper, PVDF membrane, gel and filter paper, and it was required that there was no air bubble on the contact surface. Then the system was covered and the transfer was conducted at 24 V for 30 min (the transfer time depended on the molecular weight of the target protein).

4) After the transfer was completed, a PBST solution containing 5% skim milk powder was added to block the membrane at room temperature for 1 h.

5) The PVDF membrane was placed in a western blot bag with suitable size, added with primary antibody (prepared by anti-AURKB (Abcam) and 5% skim milk powder in a ratio of 1:1,000) in an appropriate ratio, and shaken at 4° C. overnight.

6) The PVDF membrane was transferred and washed 4 times with PBST for 10 min each. Then the PVDF membrane was added with secondary antibody (prepared by anti-Rabbit (Sigma) and a PBST solution in a ratio of 1:2,000) in an appropriate ratio and incubated at room temperature for 2 h. The PVDF membrane was washed 4 times again with PBST for 10 min each.

7) Liquid A and liquid B were mixed uniformly in a ratio of 1:1 to prepare an ECL solution. The PVDF membrane was placed face up on an EP glove, added with the ECL solution and kept for 1 min. Then the ECL solution was removed, and the PVDF membrane was packed face up in the western blot bag and placed in a tablet holder for development.

8) In the developing room, an X-ray film with appropriate size was obtained by cutting and placed in an X-ray cassette, and then the cassette was closed.

9) After exposed for a suitable period of time, the X-ray cassette was opened and the X-ray film was placed in a developing solution for development. After obvious bands were observed, the film was placed in a fixing solution for fixing, washed with water and dried in an oven for the analysis.

Example 2 Biosynthesis Route of TZ47

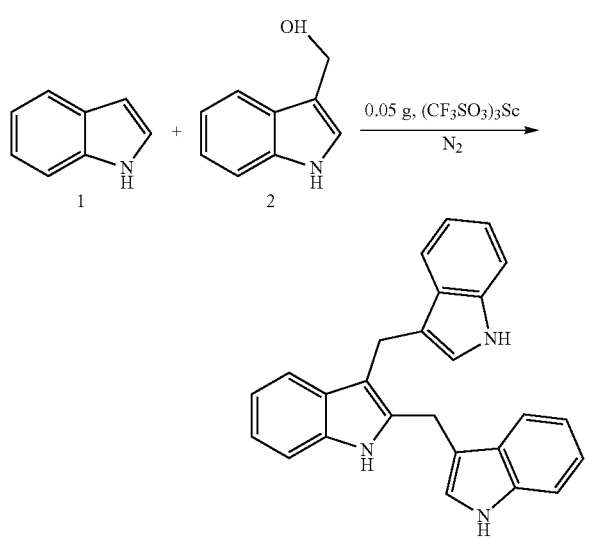

80 mg (0.68 mmol) of compound 1 and 202 mg (1.37 mmol) of compound 2 were dissolved in 6 mL of $CH_2Cl_2$, added with 0.05 g of $(CF_3SO_3)_3Sc$ and reacted under rotation in the argon atmosphere overnight to produce TZ47 (compound 3).

1H-NMR (400 MHz, acetone-d6): 10.21 (1H, brs), 10.05 (1H, brs), 9.80 (1H, brs), 7.61 (1H, d, 8.0), 7.46 (1H, d, 8.8), 7.41 (1H, d, 8.0), 7.36 (2H, d, 8.0), 7.22 (1H, d, 8.0), 7.13 (1H, s), 7.06 (2H, t, 8.0), 6.95 (2H, t, 8.0), 6.95 (1H, s), 6.88 (2H, t, 8.0), 4.32 (4H, s). 13C-NMR (400 MHz, acetone-d6): 137.8, 137.6, 136.8, 136.7, 135.6, 129.9, 128.6, 128.3, 124.0, 123.4, 122.1, 121.9, 121.0, 119.6, 119.5, 119.4, 119.2, 119.1, 119.0, 116.2, 113.4, 112.1, 112.0, 111.4, 111.4, 110.5, 23.0, 20.8.

Example 3 Inhibition of TZ47 on the Growth of Lung Cancer Cells

Figure 3:
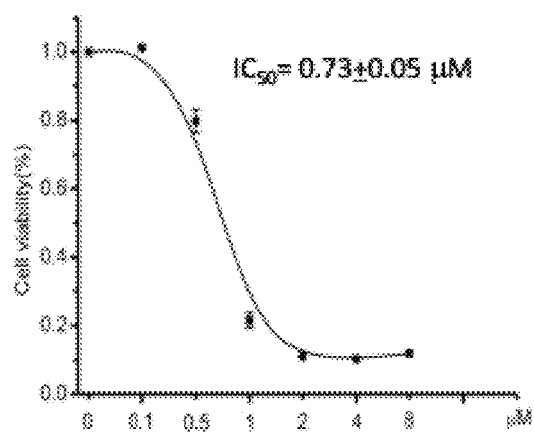
FIG. 3 shows the inhibition of the small-molecule AURKB inhibitor TZ47 on the growth of lung cancer cells by CCK-8 analysis.

Lung cancer cells A549 were separated into a 96-well plate and respectively added with 10 mM TZ47 stock solution to final concentrations of 0 µM, 0.1 µM, 0.5 µM, 1 µM, 2 µM, 4 µM and 8 µM in respective wells. Then the 96-well plate was incubated at 37° C. for 48 h and the growth of the cells was analyzed by a CCK-8 method. As shown in FIG. 3, the inhibition of TZ47 against the A549 cells was concentration-dependent and the $IC_{50}$ of TZ47 against A549 was 730 nM, which was relatively low, indicating that TZ47 has strong inhibitory activity against the A549 cells. It can be seen from Table 1 that TZ47 also plays a desirable role in inhibiting the growth of other cancer cells including colorectal cancer, leukemia, liver cancer, melanoma, breast cancer and ovarian cancer.

Example 4 Reduction of TZ47 on the Phosphorylation Level of H3S10 in Cells

Figure 4:
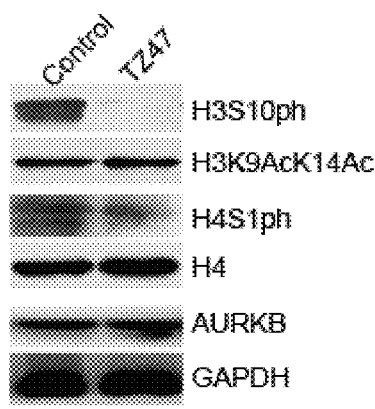
FIG. 4 shows the inhibition of the small-molecule AURKB inhibitor TZ47 on the activity of AURKB in A549 cells by Western blot assay.

A549 cells were incubated and treated with different concentrations of TZ47 for 48 h. Then the cells were collected for western blot assay, where various histone-labeled antibodies were used in the detection of the change of respective histone modifications. As shown in FIG. 4, the results indicated that the TZ47 treatment significantly reduced the phosphorylation level of H3S10 in A549 cells were, but did not mediate the degradation of AURKB protein and reduce the modification level of H4S1 ph and other histones. Therefore, it is confirmed by such results that TZ47 can inhibit the modification level of the endogenous H3S10 ph in A549 cells.

Example 5 Inhibition of TZ47 Against the Activity of AURKB In Vitro

Figure 5:
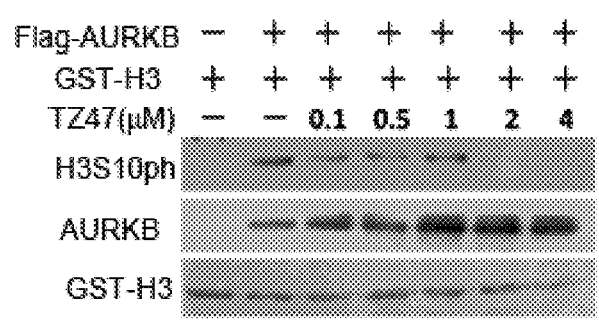
FIG. 5 shows the dissociation constant of the small-molecule AURKB inhibitor TZ47 binding with AURKB protein in vitro by MST technology.
Figure 6A:
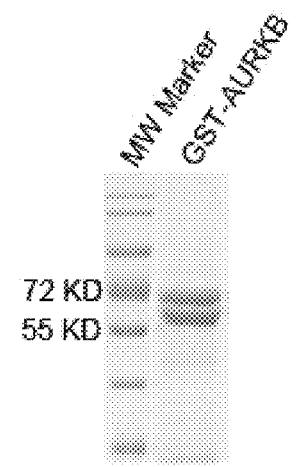
FIGS. 6A-6B show the inhibition of the small-molecule AURKB inhibitor TZ47 on the activity of AURKB in vitro by in vitro phosphorylation analysis.
Figure 6B:
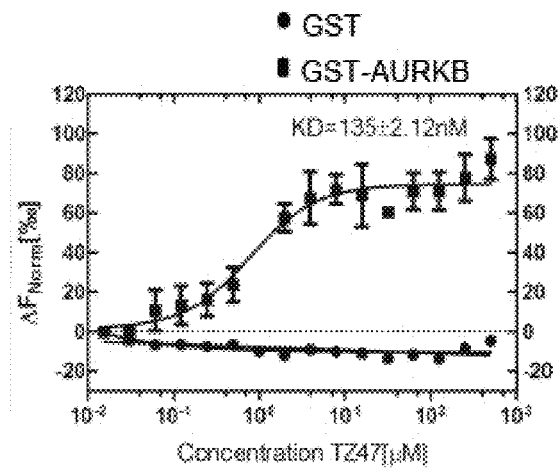

In A549 cells, TZ47 treatment can reduce the modification level of H3S10 ph, while failed to affect the labeling of other histone residues close to H3S10. Thus, it is speculated that the treatment affected the activity of a kinase which was able to phosphorylate the H3S10. The following procedures were conducted to verify whether TZ47 inhibited the activity of AURKB directly. First, prokaryotic expression of AURKB protein and purification were performed and then a microscale thermophoresis (MST) was used to detect the binding between TZ47 and AURKB protein by testing the change of microscale thermophoresis caused by the hydrated layer (generally derived from the change of the structure/conformation of biomolecules) based on the directional movement of particles in a microscopic temperature gradient. As shown in FIG. 5, results of the in vitro binding test indicated that TZ47 bound directly to the AURKB protein with a dissociation constant of 135±2 nM, and did not bind to the control GST protein. Since the prokaryotically-expressed AURKB protein showed no kinase activity, an AURKB eukaryotic expression vector pcDNA-AURKB-Flag was constructed to transfect the 293T cells. Flag-tagged AURKB protein was then enriched by M2-flag beads (anti-Flag antibody conjugated) from the lysed liquid of 293T cells and used in the in-vitro kinase activity analysis. It can be seen from FIGS. 6A-6B that the Flag-AURKB protein had kinase activity and can phosphorylate histone H3. More importantly, compared to the control group, TZ47 significantly inhibited the activity of AURKB, specifically, the kinase activity of AURKB was completely inhibited in the presence of 2 µM of TZ47. The above results demonstrated that the small molecule TZ47 was an AURKB inhibitor.

Specific steps were described as follows.
a. Expression of GST-AURKB prokaryotic protein
1) Construction of recombinant plasmid
A pGEX-6p-1 vector was used to construct a pGEX-6p-1-AURKB prokaryotic expression vector. BamH I and Xho

TABLE 1

| | IC50 (µM) of TZ47 against different tumor cells | | | | | | |
|---|---|---|---|---|---|---|---|
| Com- | Cell lines | | | | | | |
| pound | SW480 | HL-60 | HepG-2 | A375 | MCF-7 | CaoV-3 | A549 |
| TZ47 | 9.43 ± 0.34 | 0.0916 ± 0.0022 | 2.18 ± 0.12 | 1.40 ± 0.11 | 1.87 ± 0.15 | 4.47 ± 0.12 | 0.73 ± 0.24 |

I were treated as the restriction enzyme cutting sites and the PCR primers involved in the construction were shown as follows:

```
Forward:
                                      (SEQ ID NO: 1)
5'-CGCGGATCCATGGCCCAGAAGGAGAACTCC-3';

Reverse:
                                      (SEQ ID NO: 2)
5'-CGCCTCGAGTCAGGCGACAGATTGAAGGGC-3'.
```

The cDNA of 293T cells of human was used as the template to amplify the AURKB CDS sequence in the presence of LATaq enzyme. The amplified fragment and the pGEX-6p-1 vector were treated by double endonuclease digestion and used in the ligation of the recombinant plasmid. The ligated products were transformed into DH5α competent bacteria cells, and then the cells were spread on a LB plate with ampicillin resistance to select positive clones for sequencing. The plasmid having a correct sequence was the pGEX-6p-1-AURKB recombinant plasmid.

2) Expression of prokaryotic protein

The positive recombinant plasmid pGEX-6p-1-AURKB was electrotransformed into BL21 competent bacterial cells to construct prokaryotically-expressing cells. The prokaryotically-expressing cells were inoculated into 3 mL of LB medium in a ratio of 100:1 for incubation. On the next day, the bacterial cells underwent an enlarged culture in a ratio of 1:200, and after 3 h, 1 mL of the bacterial suspension was collected to measure the OD 600. When the OD 600 reached 0.6, IPTG (0.2 g/ml) can be introduced at a ratio of 1:10000 to induce the expression of AURKB prokaryotic protein. After cultured for further 4 h, the bacterial suspension was centrifuged at a high speed to collect bacterial cells which were then stored at −30° C. for use.

3) Purification of GST-AURKB protein

The bacterial cells were resuspended with PBS in a ratio of 1 L (bacterial suspension):50 mL (PBS), placed on ice and ultrasonicated at 600 W for 30 min for cell disruption, where the ultrasonication process was performed at an interval of 2 s and each sonication lasted 4 s. At the end of the ultrasonic treatment, the disrupted cells were added with Triton X-100 to a final concentration of 1%, placed at 4° C. for 30 min for solubilization and then centrifuged at 12,000 rpm and 4° C. for 15 min. The supernatant was collected to a new 50 mL tube, added with a certain amount of GST beads into the tube, rotated at 4° C. for 1 h for binding and then centrifuged at 3,000 rpm and 4° C. for 3 min. The supernatant was discarded and the cells were washed 3 times with 300 NETN solution for 1 mL each, and then an appropriate amount of GST beads were subjected to the SDS-PAGE identification.

4) Elution of GST-AURKB prokaryotic recombinant protein

A reduced glutathione eluent was prepared as follows.

| 1M Tris-HCl (pH = 8.0) | 500 μL |
| ddH₂O | added to 10 mL |
| L-glutathione | 0.03 g |

1 mL of the eluent was added to the EP tube containing GST beads, rotated at 4° C. for 30 min and centrifuged at 3,000 rpm for 3 min. The supernatant was collected. The elution was repeated twice, and the supernatants were combined (namely the GST-AURKB solution) and stored at −80° C. An appropriate amount of the combined supernatant was subjected to SDS-PAGE for the determination of elution efficiency and protein purity and quantity.

b. Microscale thermophoresis test (MST test)

MST test was carried out to verify the direct interaction between TZ47 and AURKB, and the specific steps were as follows.

a) Buffer exchange

It was required in the labeling process that the protein was dissolved in a labeling buffer with appropriate pH. Moreover, since the primary amine compounds (e.g., ammonium ion, Tris, glycine, ethanolamine, triethylamine, glutathione) and imidazole may significantly reduce the efficiency of protein labeling, these compounds should be absent in the buffer. Low protein purity or carrier proteins such as BSA contained in protein samples may affect the protein labeling. The specific operations were described as follows.

1) 3 mL of double distilled water was added to dissolve the buffer salt in a vial.
2) The mixing column A was inverted with the cover at the bottom twisted off and the column cover unscrewed.
3) The column was placed in a 1.5-2 mL EP tube and centrifuged at 3,000 rpm for 1 min to remove excess liquid in column A. Then the column A was added with 300 μL of a labeling buffer solution and centrifuged at 3,000 rpm for 1 min to wash the column, and this process was repeated 3 times.
4) 40-100 μL of the protein solution was added to the column A, and then the column A was transferred to a new EP tube, and centrifuged at 3,000 rpm and 4° C. for 2 min to complete the exchange of the buffer in the protein solution.

b) Labeling of protein

1) The protein solution was adjusted with the labeling buffer to a concentration of 2-20 μM.
2) 50 μL of DMSO was added to dissolve a solid dye (the concentration of the dye was about 650 μM).
3) The dye was mixed uniformly with DMSO for complete dissolution, and then the dye solution was diluted with the labeling buffer to a concentration which was 2-3 times the concentration of protein.
4) The dye solution was mixed with the protein solution in a volume ratio of 1:1 and incubated at room temperature in the dark for 30 min. Step 2.18.3 was simultaneously prepared.

c) Purification of protein

Unreacted free dye was required to be removed by passing through a column to optimize the test results of MST. The purity of the labeled protein can be obtained by measuring the ratio of the protein to the dye (for example, the ratio can be obtained by measuring the absorbance of protein at 280 nm and dye at 650 nm, where the molar absorbance was 250 $M^{-1}$ $cm^{-1}$).

1) The column B was emptied and equilibrated with a protein stock buffer or the test solution which was used in the final MST test (a total of 8 mL of the solution was needed; and the buffer naturally passed through the column B to complete the equilibration).
2) 200 μL of a labeling reaction solution was added to completely immerse the column B and then the effluent was discarded.
3) 300 μL of the flushing solution was added to completely immerse column B and then the effluent was discarded.

4) 600 µL of the flushing solution was added to the column B and the eluted liquid was collected (the first two drops of liquid can be discarded).
5) The ratio of protein to dye was measured by spectrometry and the proteins were sub-packaged.

d) MST reaction

The TZ47 small molecule mother solution was diluted sequentially in doubling dilution manner and a total of 16 PCR tubes containing different concentrations of TZ47 were finally obtained. The solution in respective tubes was mixed with the protein labeled in step (c) in a volume ratio of 1:1 and adsorbed by a capillary to its top, where the formation of bubble in the capillary should be avoided. After that, the capillary was transferred to a Nano Temper MST instrument for the reading of the fluorescence value, and then the dissociation constant KD was calculated based on the fluorescence value using the instrument software program.

c. In vitro phosphorylation

TABLE 2

| In vitro phosphorylation system | |
|---|---|
| GST/GST-histone H3 | 1 µg |
| Active AURKB | 0.5 µg |
| Tris-HCl (pH = 7.5) | 25 mM |
| β-glycerophosphate | 5 mM |
| DTT | 2 mM |
| $Na_3VO_4$ | 0.1 mM |
| $MgCl_2$ | 10 mM |
| $MnCl_2$ | 5 mM |
| ATP | 100 µM |
| TZ47 | 0.01-2 µM |

The components were mixed according to the above specifications, and reacted at 30° C. for 30 min. After the reaction was completed, the reaction mixture was subjected to western blot assay.

Example 6

A stable AURKB-knockdown non-small lung cancer cell strain was constructed, and it was detected that the modification level of H3S10 ph was reduced.

Figure 7A:
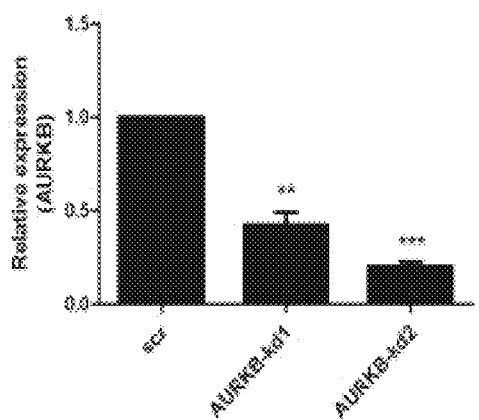
FIGS. 7A-7B show the construction and detection of an AURKB-knockdown A549 cell strain.
Figure 7B:
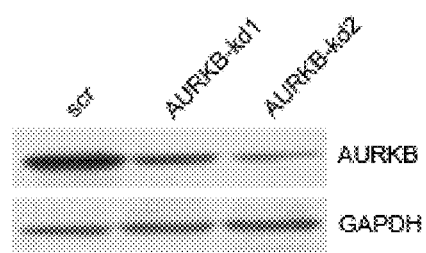
Figure 8:
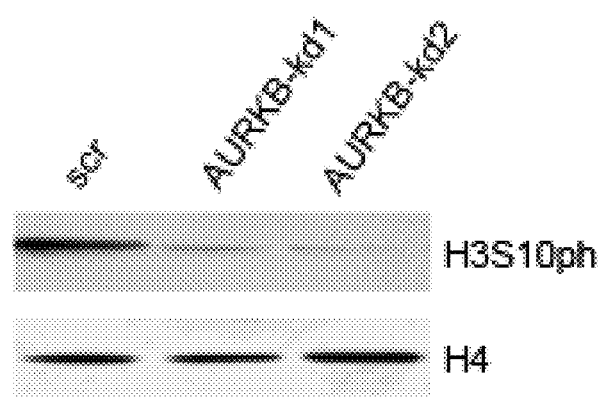
FIG. 8 shows the reduction in the phosphorylation level of H3S10 in the AURKB-knockdown A549 cell strain by Western blot assay.

The stable AURKB-knockdown A549 cell strain was constructed using shRNA lentiviral system to confirm whether AURKB directly phosphorylated the histone H3S10 site in non-small cell lung cancer cells. The expression levels of AURKB were analyzed by real-time quantitative PCR and western blot assay (see FIGS. 7A-7B). The results showed that the expression levels of both mRNA and protein of AURKB were significantly downregulated. Meanwhile, it was also demonstrated by the western blot assay that the modification level of H3S10 ph was significantly reduced. The results verified that H3S10 was the histone substrate of AURKB (see FIG. 8).

The detailed steps were described as follows.

1) Construction and detection of stable A549 cell strain of AURKB-knockdown non-small cell lung cancer cells The stable AURKB-knockdown A549 cell strain was constructed using the pLL3.7 shRNA lentiviral system. A549 cells were purchased from Shanghai Institute of Cell Biology and incubated in a DMEM (V/V, Thermofisher) containing 10% FCS. The siRNA target sequence of AURKB was inserted into the XhoI/HpaI sites of the pLL3.7 lentiviral plasmid following the manufacturer's instructions. The shRNA targets were shown as follows:

```
Human AURKB shRNA1:
                                      (SEQ ID NO: 3)
GGTGATTCACAGAGACATA Human AURKB shRNA2:
                                      (SEQ ID NO: 4)
CGCTCAAGGTCCTCTTCAA
```

2) Detection of expression levels of AURKB gene's mRNA in SCR control cells and AURKB-knockdown cell strains (AURKB-kd1 and AURKB-kd2) by real-time quantitative PCR The detailed steps were described as follows.

a. Extraction of total RNA from cells

1) The cell density was determined by the plate counting method (cells in the grids at the four corners and the middle were counted and averaged, and the cell density was required to reach $5 \times 10^6$ cells/mL).
2) 7 mL of cell solution was added to a 15 ml sterile centrifuge tube in a biosafety cabinet and centrifuged at 1,000 rpm for 10 min.
3) The supernatant was removed, and the cells were suspended with 1 mL of PBS and then transferred to an EP tube (the EP tubes and the Tip heads used below must be treated with 0.1% DEPC water and sterilized by moist heat before use).
4) The supernatant was removed, and the cells were suspended with 1 mL of PBS and centrifuged at 3,000 rpm for 5 min.
5) The supernatant was discarded, and the cells in respective tubes were suspended with 1 mL of Trizol completely till the cell solution was transparent and left for a standing at room temperature for 5 min.
6) The solution was additionally added with 200 µL of chloroform, shaken vigorously for 15 s, and then left for a standing at room temperature for 2-3 min.
7) The solution was centrifuged at 12,000×g and 4° C. for 15 min.
8) The upper aqueous phase (about 600 µL) was pipetted, transferred to a new EP tube, added with 500 µL of isopropanol and left for a standing at room temperature for 10 min.
9) The solution was centrifuged at 12,000×g and 4° C. for 10 min.
10) The supernatant was removed, and the precipitate was added with 1 mL of pre-cooled 75% ethanol (prepared by 0.1% DEPC water) and shaken for a while.
11) The solution was centrifuged at 7500×g and 4° C. for 5 min.
12) The supernatant was removed, and the precipitate was dried, dissolved in 20 µL of 0.1% DEPC water, placed at 55° C. for 10 min for solubilization and measured by spectrophotometer for the concentration and purity. The RNA can be directly used for the reverse transcription of cDNA or stored at −80° C. for use.

b. cDNA synthesis

1) HiScript Reverse Transcriptase system

TABLE 3

| HiScript Reverse Transcriptase system in an RNase-free EP tube | |
|---|---|
| RNase free dd$H_2O$ | to 8 µL |
| 4 × gDNA wiper Mix | 2 µL |
| Template RNA | Total RNA: 1 pg~500 ng |

The above mixture was mixed uniformly with a pipette and heated 42° C. for 2 min. Then the mixture was further added with 5×qRT SuperMix II and mixed uniformly with a pipette. The cDNA was synthesized as follows: 25° C. for 10 min; 50° C. for 30 min and 85° C. for 5 min. The synthesized cDNA had a sequence as shown in SEQ ID NO: 5.

The product can be immediately used in the PCR reaction or stored at −20° C. for use.

The Q-RT-PCR test was carried out using the Corbett Rotor-gene 6000 quantitative PCR instrument (Gene Company Limited). The reagent used in the test was Roche FastStart Universal SYBR Green Master Mix. The reaction system was shown below.

TABLE 4

| Conditions for Q-RT-PCR reaction | |
|---|---|
| SYBR Green Mix | 10 μL |
| Forward Primer (50 μM) | 0.5 μL |
| Reverse Primer (50 μM) | 0.5 μL |
| cDNA | 2 μL |
| ddH2O | 7 μL |

The Q-RT-PCR reaction conditions were described as follows: pre-denaturation at 95° C. for 10 min; 40 cycles and one cycle consisting of denaturation at 95° C. for 20 s and annealing at 60° C. for 25 s; and extension at 72° C. for 20 s (fluorescence signal acquisition).

TABLE 5

Primers for AURKB and E2F2 genes

| Gene | Forward (5'-3') | Reverse (5'-3') |
|---|---|---|
| AURKB | ACATCTTAACGCGGCACTTC (SEQ ID NO: 6) | ATGAAATGGCTTTTCTTCTCC (SEQ ID NO: 7) |
| E2F2 | AGACTCGGTATGACACTTC (SEQ ID NO: 8) | CACTGGATGTTGTTCTTGG (SEQ ID NO: 9) |

Figure 9A:
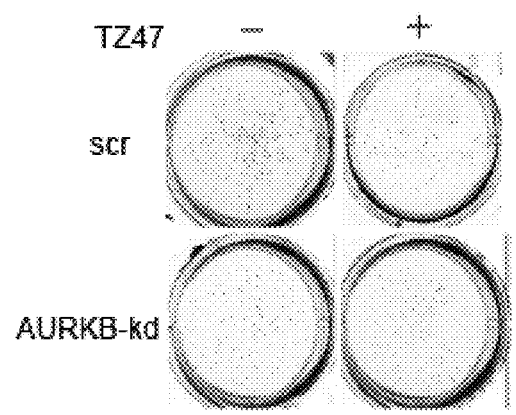
FIGS. 9A-9B show the significant inhibition of the small-molecule AURKB inhibitor TZ47 on the clonogenicity of A549 cells by colony formation assay.
Figure 9B:
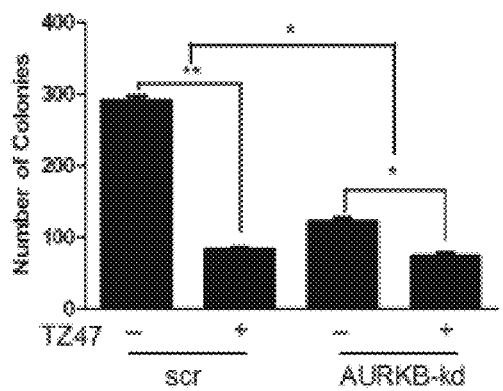

Example 7 Inhibition of TZ47 on the Proliferation and Migration of Lung Cancer Cells Colony-formation assay was performed to examine the effect of TZ47 on the cell proliferation. The results showed that the knockdown of AURKB can significantly reduce the cell colony formation ability. In addition, the colony formation in the control cells was also significantly inhibited after treated with TZ47 (2 μM) (FIGS. 9A-9B). These results indicated that TZ47 can inhibit the activity of AURKB to further inhibit the proliferation of cells.

Figure 10A:
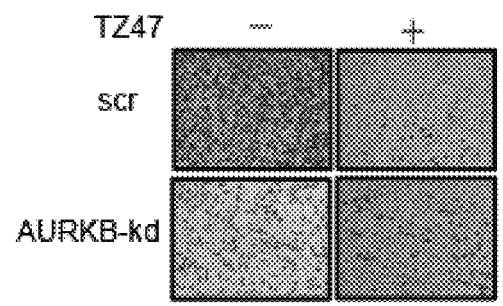
FIGS. 10A-10B show the significant inhibition of the small-molecule AURKB inhibitor TZ47 on the migration ability of A549 cell by Transwell assay.
Figure 10B:
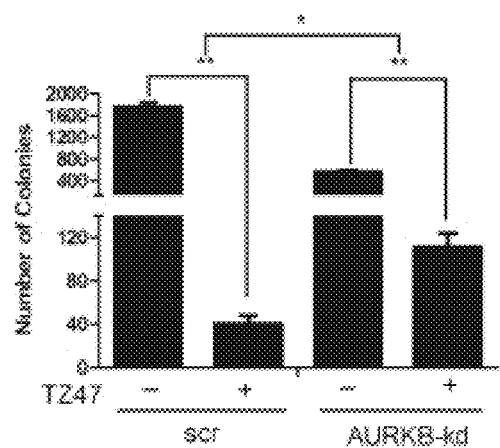

In addition, Transwell test was also conducted to determine the effect of the expression level of AURKB on the cell migration ability. Similarly, TZ47 (2 μM) was used to treat cells in the Transwell test. It was confirmed by the results that the knockdown of AURKB significantly inhibited the migration ability of cells and TZ47 also significantly showed inhibitory effect on the migration ability of cells. At the same time, compared to the control scr cells, AURKB-kd cells can partially antagonize the inhibitory effect of TZ47 on cell migration (FIGS. 10A-10B). It can be seen from the above results that TZ47 showed an inhibitory effect on the migration ability of cells. The specific steps were described as follows:

a. Cell migration test
1) The cells to be tested in the logarithmic growth phase was digested with trypsin and centrifuged to collect the cells. Then the cells were washed once with PBS and resuspended with serum-free DMEM for counting.
2) 500 μl, of DMEM medium containing 10% FBS was added to a 24-well plate and a Transwell chamber was carefully placed into the plate to prevent air bubbles. Then 100 μL of cell suspension (about 50,000 cells) was added to the Transwell chamber, and a TZ47 solution (final concentration: 2 μM) was simultaneously added to the TZ47 treatment group. The 24-well plate was incubated at 37° C. and 5% CO₂ in a cell incubator for 12 h.
3) The Transwell chamber was removed from the plate and washed in PBS to remove the medium. PBS in the chamber was adsorbed and 500 μL of methanol was added to the chamber to fix the cells at room temperature for 30 min.
4) The chamber was taken out, washed once with PBS and stained in 0.1% crystal violet staining solution for 30 min.
5) The chamber was taken out and washed once with PBS, and the PBS on the chamber was absorbed. The cells on the inner membrane surface of the chamber were carefully wiped with a cotton swab.
6) The chamber was placed on a glass slide and observed to count the number of cells on the outer membrane.

b. Cell colony formation assay
1) The cells to be tested in the logarithmic growth phase was digested with trypsin and centrifuged to collect the cells. Then the cells were washed once with PBS and resuspended with serum-free DMEM for counting.
2) Respective wells of a 6-well plate were added with 2 mL of DMEM containing 10% FBS and then added with 500 cells. Moreover, respective wells of the TZ47-treatment group were further required to be added with a TZ47 solution to a final concentration of 2 μM. The 6-well plate was incubated at 37° C. and 5% CO₂ in a cell incubator for 2 weeks.
3) The plate was transferred from the incubator and the medium was removed. The plate was washed once with PBS and then the PBS in the plate was adsorbed. 1 mL of methanol was added to respective wells to fix the cells at room temperature for 30 min.
4) The methanol was removed, and the plate was washed once with PBS. 1 mL of 0.1% crystal violet staining solution was added to respective wells for staining for 30 min. Then the staining solution was removed and the plate was washed once with PBS. The PBS remained in the plate was absorbed and the plate was naturally dried and used for the counting of the number of clones in respective wells.

Example 8 Inhibition of TZ47 on the Expression of Gene E2F2

Figure 11:
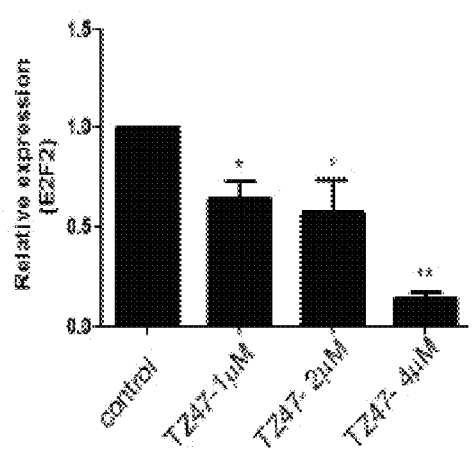
FIG. 11 shows significant inhibition of the small-molecule AURKB inhibitor TZ47 on the expression of mRNA of E2F2 in A549 cells by real-time quantitative PCR analysis.
Figure 12:
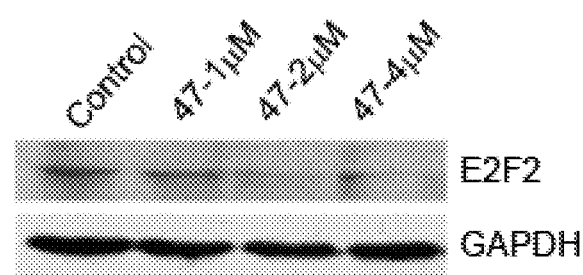
FIG. 12 shows the inhibition of the small-molecule AURKB inhibitor TZ47 on the expression of the protein of E2F2 in A549 cell by Western blot analysis.
Figure 13A:
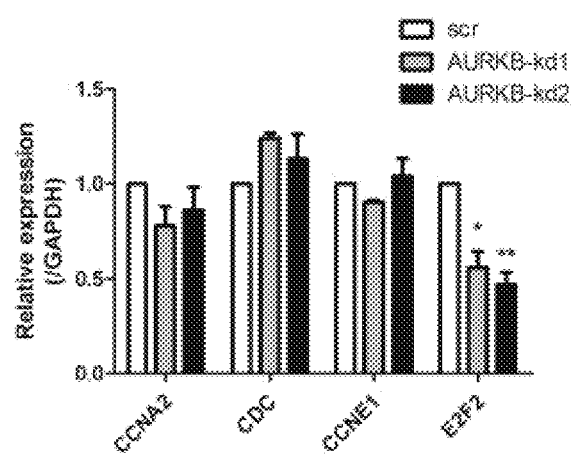
FIGS. 13A-13B show that the knockdown of AURKB is confirmed by real-time quantitative PCR and Western blot to lower the expression of mRNA and protein of gene E2F2.
Figure 13B:
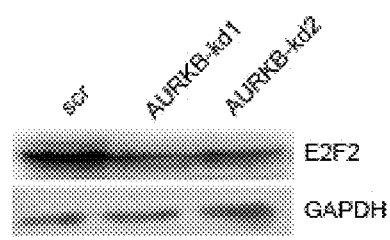
Figure 14:
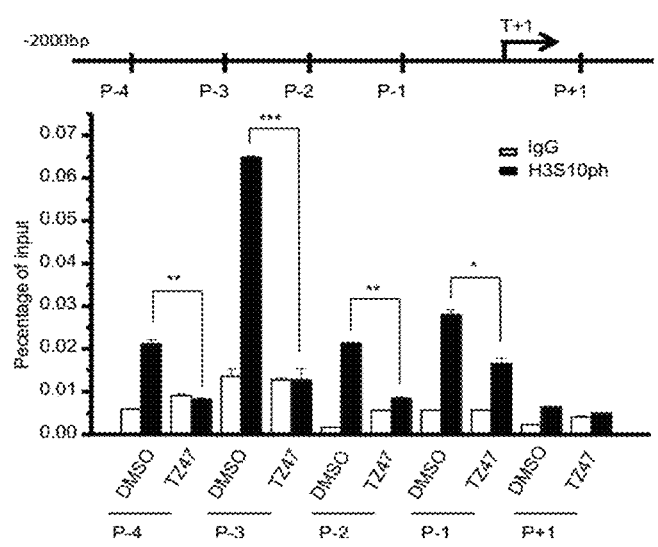
FIG. 14 shows that the enrichment of H3S10 ph marker near the promoter of E2F2 in the A549 cells is lowered by the small-molecule AURKB inhibitor TZ47 as demonstrated by the ChIP assay.

A549 cells were treated by different concentrations of TZ47, and then total RNAs and total proteins of cells were extracted to detect the expression of gene E2F2. Real-time quantitative PCR test results showed that, compared to the control cells, the expression level of gene E2F2 in the cells treated with TZ47 was also significantly reduced (FIG. 11). Moreover, the Western blot test results also indicated that the protein level was reduced by TZ47 (FIG. 12). At the same time, the detection results of the AURKB-knockdown cells were consistent with the above results (FIGS. 13A-13B), which indicated that TZ47 can regulate the expression of gene E2F2 in cells by inhibiting the activity of AURKB. To further verify the above results, A549 cells were treated with TZ47 and extracted for chromatin, and the chromatin and an H3S10 ph-specific antibody were then used in the ChIP assay. The test results showed that the enrichment of histone H3S10 ph near the E2F2 promoter was significantly reduced in TZ47-treated A549 cells (FIG. 14). It can be seen from the above tests that TZ47 can inhibit the AURKB activity and further inhibit the level of AURKB histone substrate H3S10 ph on the promoter of gene E2F2, affecting the expression of gene E2F2.

The specific steps were described as follows.

a. Detailed steps and conditions for Western blot assay and real-time quantitative PCR test have been described in the above Examples.

b. Chromatin co-immunoprecipitation (ChIP)

1) In vivo cross-linking of DNA-protein complex $2 \times 10^{6-7}$ cells were collected by low-speed centrifugation, resuspended in 20 mL of RPMI 1640 medium, added with 550 µL of a 37% formalin solution in a fuming cupboard to a final concentration of 1% and incubated for 10 min. The system was mixed 2-3 times during the incubation.

2) Termination of cross-linking

The cross-linking system was added with 1.35 mL of 2 M glycine (final concentration: 0.1 M), mixed uniformly and incubated for 10 min. The system was mixed 2-3 times during the incubation. Then the system was centrifuged at 2,400 rpm for 7 min, and the supernatant was discarded. The cells were washed twice with 10 mL of a pre-cooled PBS solution. After centrifuged, the cells were placed on ice.

3) Preparation of cell nucleus

The cells were added with 1 mL of TNT buffer (10 mM Tris-HCl pH 8.0, 10 mM NaCl, 0.2% Triton X-100, 1×protease inhibitor), placed on ice for 10 min and centrifuged at 2,400 rpm for 7 min. The supernatant was discarded and the nucleus can be frozen at −80° C.

4) Nucleus lysis and chromatin fragmentation

The nucleus was added with 1 mL of NB buffer (50 mM Tris-Cl pH 8.0, 10 mM EDTA, 1×protease inhibitor), placed on ice for 10 min and mixed uniformly by vortex. The lysate was ultrasonicated at 200 W 7 times with 20 s for each and at the interval between the two adjacent ultrasonications, the sample should be placed on ice for more than 2 min to make it cool. Then the sample was added with 1/10 volume of 10% SDS solution, mixed at room temperature for 1 h and centrifuged at 14,000 rpm and 4° C. for 10 min. The supernatant was collected and used in the agarose gel electrophoresis to identify whether the size of the band was within the range of 200 bp-1000 bp. The ultrasonication was still required If the band was too large.

5) Co-immunoprecipitation

The $OD_{260}$ value of the supernatant was determined and used to calculate the DNA concentration. The supernatant containing 100 µg of DNA was transferred, added with 700 µL of DB buffer (150 mM NaCl, 20 mM Tris-HCl pH 8.0, 2 mM EDTA, 1% Trion X-100 and 1×protease inhibitor), further added with 2 µg of IgG or the antibody used in the test group, rotated at 4° C. for 2 h and centrifuged at 12,000 rpm and 4° C. for 10 min. The supernatant was transferred to a new EP tube, added with 50 µL of Protein A/G sepharose beads, and rotated at 4° C. overnight to allow the antibody to fully couple with Protein A/G sepharose beads, where the Protein A/G sepharose beads were blocked with 1 mg/mL salmon sperm DNA and 1 mg/mL BSA at 4° C. for 2 h, washed with DB buffer twice and resuspended with DB buffer in a ratio of 1:1 in advance.

6) Washing

The system was centrifuged at 3,000 rpm and 4° C. for 3 min, and the precipitate was washed as follows: 1 mL of RIPA 150 (10 mM Tris-HCl (pH 8.0), 150 mM NaCl, 1% Triton X-100, 0.1% SDS, 1% deoxycholic acid) once;

1 mL of RIPA 500 (10 mM Tris-HCl (pH 8.0), 500 mM NaCl, 1% Triton X-100, 0.1% SDS, 1% deoxycholic acid) twice;

1 mL of LIDS (LiCl detergent solution, 250 mM LiCl, 1 mM EDTA, 10 mM Tris-HCl (pH 8.0), 1% NP-40, 1% deoxycholic acid) 5 times; and 1 mL of TE (10 mM Tris-HCl (pH 8.0), 1 mM EDTA) twice.

7) Elution of the co-immunoprecipitated complex

The co-immunoprecipitated complex was added with 200 µL of TE solution containing 1% SDS, mixed, incubated at 65° C. for 10 min and centrifuged. The supernatant was transferred to a new centrifuge tube and the above steps were repeated once. The obtained eluates were combined and centrifuged at 12,000 rpm for 1 min, and then the supernatant was transferred to a new EP tube.

12) Cross-linking reversion

10% of the chromatin in 4) was used as input and supplemented to 400 µL with a TE solution containing 1% SDS. The eluate and input tubes were respectively added with 2 µL of proteinase K (20 mg/mL) and incubated at 65° C. overnight.

13) Purification of DNA and PCR test

The mixtures in respective tubes were respectively added with 400 µL of a mixed solution of phenol, chloroform and isoamyl alcohol, mixed uniformly and centrifuged at 14,000 rpm and 4° C. for 10 min. 300 µL of the upper aqueous phase was transferred to a new EP tube, added with 2 µL of glycogen (10 mg/mL), 30 µL of 3 M sodium acetate (pH=5.2) and 600 µL of pre-cooled ethanol, mixed uniformly followed by a standing at −80° C. for at least 30 min and centrifuged at 14,000 rpm and 4° C. for 10 min. The supernatant was discarded and the precipitate was washed with pre-cooled 70% ethanol solution and centrifuged at 14,000 rpm and 4° C. for 10 min. The supernatant was discarded and the precipitate in respective tubes was dried in a vacuum centrifugal pump for 30 min and added with 50 µL of TE or deionized water for dissolution and stored at −20° C. The obtained DNAs can be used for the subsequent real-time quantitative PCR tests.

Example 9 Induction of TZ47 on the Apoptosis and Autophagy of A549 Cells

Figure 15A:
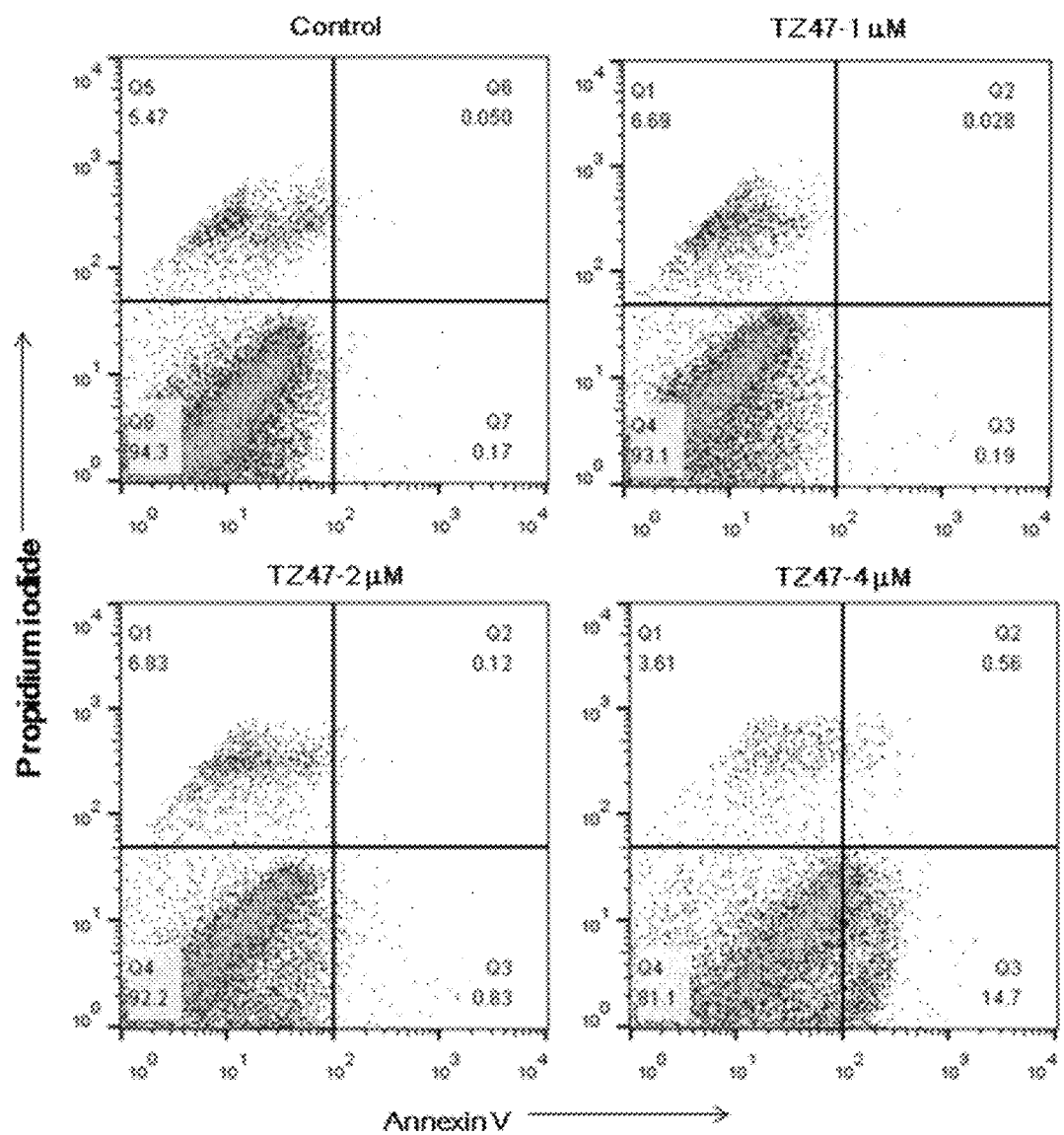
FIGS. 15A-15B show the dosage effect of the small-molecule AURKB inhibitor TZ47 on the induction of apoptosis of A549 cells.
Figure 15B:
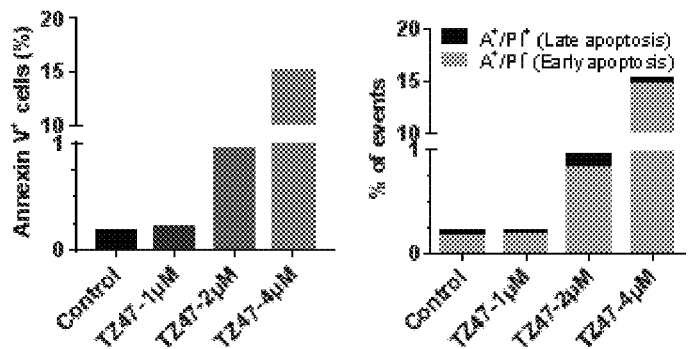
Figure 16A:
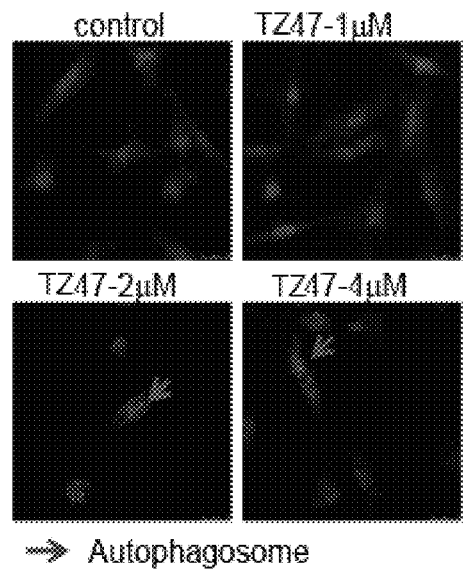
FIGS. 16A-16B show the dosage effect of the small-molecule AURKB inhibitor TZ47 on the induction of autophagy of A549 cells.
Figure 16B:
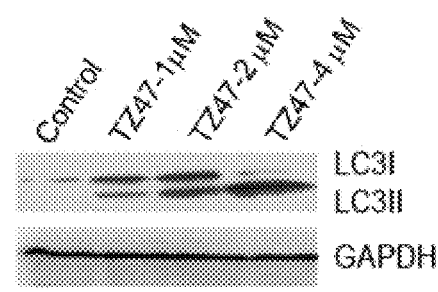

It has been confirmed before that a high concentration of TZ47 could completely inhibit the cell proliferation and induce the cell death. To elucidate how TZ47 induced the cell death, a flow cytometer was applied to measure and analyze the apoptosis of cells in solvent (DMSO) control group and the treatment groups with different gradients of TZ47 in the use of a cell apoptosis detection kit. The results showed that there was no significant difference between the 1 µM and 2 µM treatment groups with the increase in TZ47 concentration, and when the concentration reached 4 µM, the proportion of early apoptotic cells was significantly increased (FIGS. 15A-15B) In addition, it is also detected that with the increase in the concentration of TZ47, the degree of cell autophagy was also increased significantly, which was also confirmed by the western blot assay of LC3 antibody (FIGS. 16A-16B), Besides, the degree of cell autophagy was concentration-dependent from TZ47.

Figure 17:
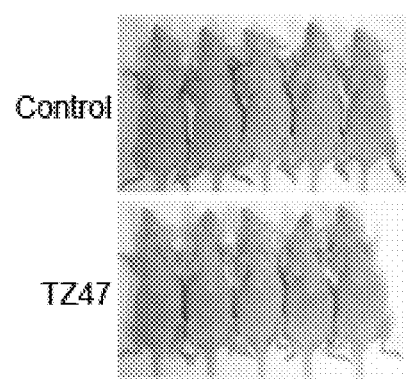
FIG. 17 shows the inhibition of the small-molecule AURKB inhibitor TZ47 on the growth of lung cancer in vivo by heterotopic xenograft assay in nude mice.
Figure 18A:
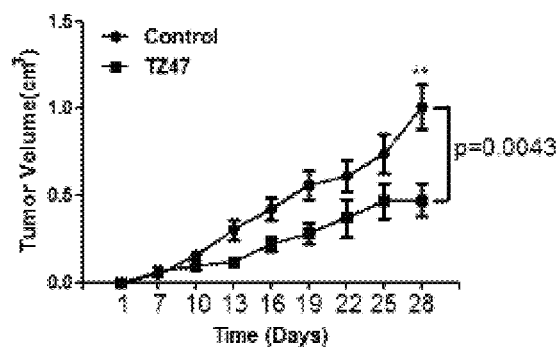
FIGS. 18A-18C show the comparison of the volumes and weights of xenografts in mice between the administration group and the control in the heterotopic xenograft assay of nude mice.
Figure 18B:
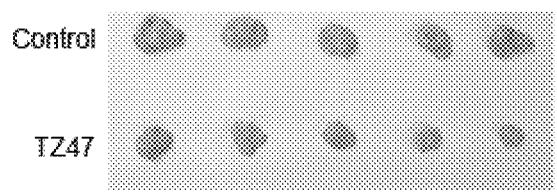
Figure 18C:
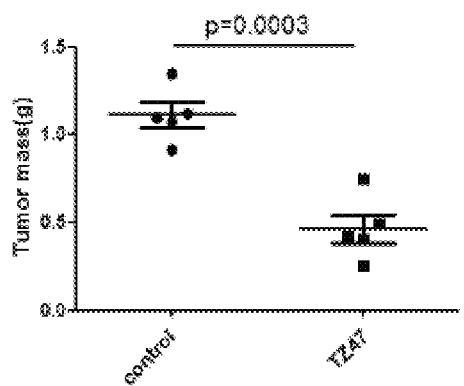
Figure 19:
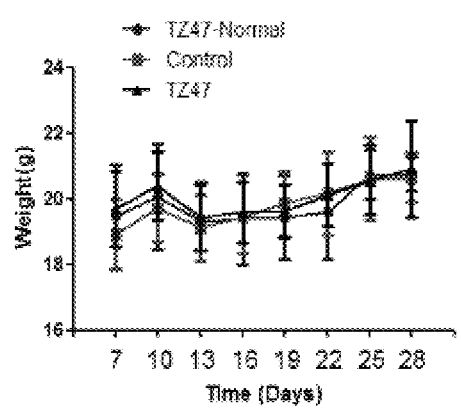
FIG. 19 shows the comparison of the volumes of mice among the TZ47-treatment normal group, the control xenograft group and the TZ47-treatment xenograft group in the heterotopic xenograft assay of nude mice.

Example 10 Inhibition of TZ47 on the Growth of Lune Cancer Cells and on the Activity of AURKB In Vivo in the Nude Mouse Xenograft Model The lung-cancer mouse model was constructed to test the effect of TZ47 on tumor proliferation in vivo. First, A549 cells were inoculated into the mice at the left axilla. When the tumor was proliferated to 100 mm$^3$, the mice were treated with TZ47 (150 mg/kg), and the weight, tumor volume and diet were observed and recorded. In the sixth week, the mice were anesthetized, and the tumors were photographed and recorded. As shown in FIG. 17, compared to the mice in the solvent control group (DMSO), the tumor volume in the TZ47-treated mice was significantly smaller, which was also confirmed by the measurement of the tumor growth curve (FIGS. 18A-18C). There was significant difference in the mice between the control group and the TZ47-treated group, while no significant difference was observed in the indexes such as behavior, diet and weight of the mice between the control group and the TZ47-treated group (FIG. 19). The mice were quickly sacrificed through the dislocation of cervical vertebra, and the solid tumor was collected and weighed. The statistical result showed that TZ47 had significant activity in inhibiting the tumor growth in vivo (FIGS. 18A-18C).

Figure 20:
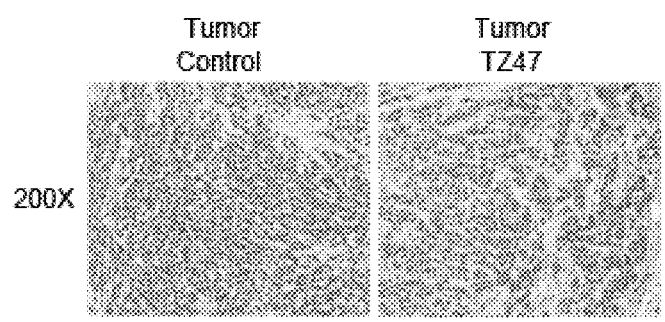
FIG. 20 is a hematoxylin and eosin (H&E) staining image showing the comparison of xenograft tissues in mice between the administration group and the control group in the heterotopic xenograft assay for nude mice.
Figure 21:
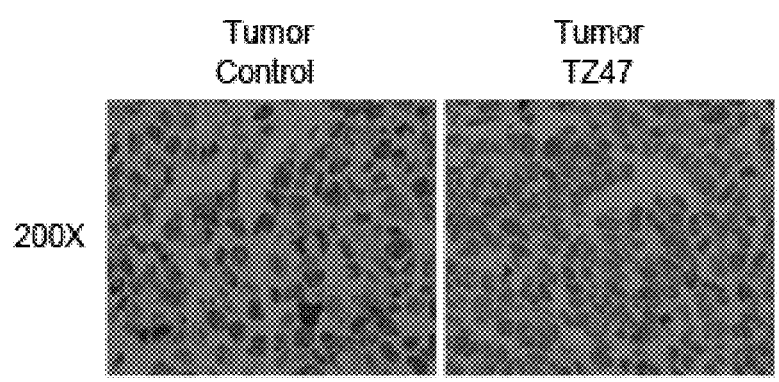
FIG. 21 shows the comparison of Ki-67 immunohistochemical staining of xenograft tissues in mice between the administration group and the control in the heterotopic xenograft assay of nude mice.
Figure 22A:
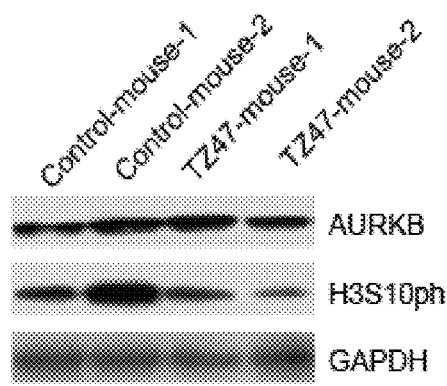
FIGS. 22A-22B show the comparison of the protein levels of histone H3S10 ph in xenograft tissues in mice between the administration group and the control group in the heterotopic xenograft assay of nude mice.
Figure 22B:
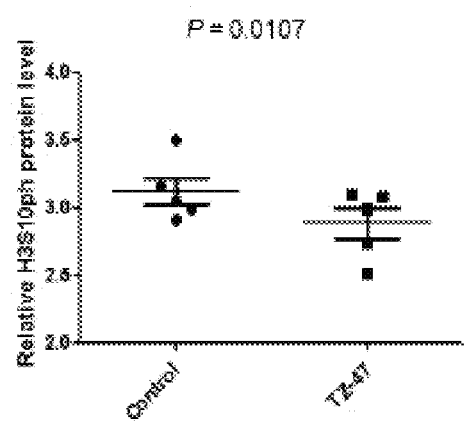

Next, part of the solid tumor was extracted for the immunohistochemistry assay. The HE staining result showed that the solid tumor cells in the control group distributed closely while the gap among the tumor cells in the TZ47-treatment group was larger due to the presence of a large quantity of necrotic tissues. Generally speaking, HE signal of the control group was significantly stronger than that of the TZ47-treatment group (FIG. 20), which was also verified by the immunohistochemistry assay with Ki-67 (FIG. 21). The solid tumor protein was lysed and analyzed by western blot assay. The results showed that TZ47 treatment did not affect the expression level of AURKB protein. Compared to the control group, the H3S10 ph modification level was significantly reduced, which was also confirmed by the overall statistical analysis (P<0.05) (FIGS. 22A-22B). These results strongly confirmed that TZ47 had an ideal molecular activity, and can inhibit the AURKB activity to reduce the H3S10 ph level in vivo, further inhibiting the proliferation of tumor cells.

What is claimed is:

1. A method of treating non-small cell lung cancer in a patient in need thereof, comprising: administering to the patient a therapeutically effective amount of a diindolylmethane compound of formula (I-a), or a solvate, an N-oxide or a pharmaceutically acceptable salt thereof,

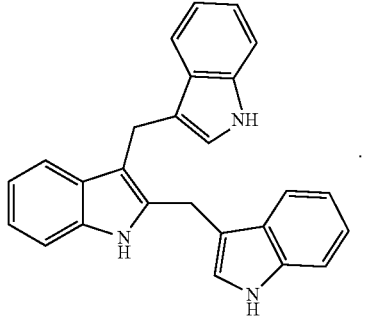

(I-a)

* * * * *